(12) United States Patent
Accomando et al.

(10) Patent No.: US 10,026,191 B2
(45) Date of Patent: Jul. 17, 2018

(54) MULTI-IMAGING MODALITY NAVIGATION SYSTEM

(71) Applicant: Analogic Corporation, Peabody, MA (US)

(72) Inventors: Nicholas A Accomando, Hingham, MA (US); David Lieblich, Worcester, MA (US); John O'Connor, Andover, MA (US); Louis Poulo, Andover, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 15/039,621

(22) PCT Filed: Nov. 27, 2013

(86) PCT No.: PCT/US2013/072154
§ 371 (c)(1),
(2) Date: May 26, 2016

(87) PCT Pub. No.: WO2015/080716
PCT Pub. Date: Jun. 4, 2015

(65) Prior Publication Data
US 2017/0169577 A1 Jun. 15, 2017

(51) Int. Cl.
*G06T 7/33* (2017.01)
*A61B 8/08* (2006.01)
*G06T 7/37* (2017.01)

(52) U.S. Cl.
CPC ............... *G06T 7/33* (2017.01); *A61B 8/085* (2013.01); *A61B 8/0841* (2013.01); *A61B 8/483* (2013.01); *G06T 7/37* (2017.01)

(58) Field of Classification Search
CPC .. G06T 7/33; G06T 7/37; A61B 8/085; A61B 8/483
(Continued)

(56) References Cited

U.S. PATENT DOCUMENTS 5,488,674 A 1/1996 Burt et al.
5,672,877 A 9/1997 Liebig et al.
(Continued)

FOREIGN PATENT DOCUMENTS

DE 10323008 A1 12/2004
WO 2011/148299 A1 12/2011

OTHER PUBLICATIONS

Peters, T., Image-guidance for surgical procedures, Physics in Medicine and Biology, 51 (2006) R505-R540.
(Continued)

*Primary Examiner* — Ruiping Li
(74) *Attorney, Agent, or Firm* — Anthony M. Del Zoppo, III; Driggs, Hogg, Daugherty & Del Zoppo Co., LPA (57) ABSTRACT

A method includes obtaining first 3D imaging data for a volume of interest. The first 3D imaging data includes structural imaging data and a target tissue of interest. The method further includes obtaining 2D imaging data. The 2D imaging data includes structural imaging data for a plane of the volume of interest. The plane includes at least three fiducial markers of a set of fiducial markers. The method further includes locating a plane, including location and orientation, in the first 3D imaging data that corresponds to the plane of the 2D imaging data by matching the at least three fiducial markers with corresponding fiducial markers identified in the first 3D imaging data and using the map. The method further includes visually displaying the first 3D imaging data with the 2D imaging data superimposed over at the corresponding plane located in the first 3D imaging data.

23 Claims, 4 Drawing Sheets

(58) Field of Classification Search
USPC .................................................... 382/285
See application file for complete search history.

(56) References Cited

U.S. PATENT DOCUMENTS

| | | | |
|---|---|---|---|
| 5,766,129 | A | 6/1998 | Mochizuki |
| 6,856,666 | B2 | 2/2005 | Lonn et al. |
| 6,966,878 | B2 | 11/2005 | Schoisswohl et al. |
| 7,483,034 | B2 | 1/2009 | Chefd'hotel et al. |
| 7,529,392 | B2 | 5/2009 | Makram-Ebeid |
| 7,639,896 | B2 | 12/2009 | Sun et al. |
| 8,111,892 | B2 | 2/2012 | Hyun et al. |
| 8,090,429 | B2 | 3/2012 | Vija et al. |
| 8,144,951 | B2 | 3/2012 | Martin et al. |
| 8,145,012 | B2 | 3/2012 | Meetz et al. |
| 8,270,691 | B2 | 9/2012 | Xu et al. |
| 8,425,418 | B2 | 4/2013 | Suri et al. |
| 8,427,475 | B2 | 4/2013 | Ruijters et al. |
| 8,369,592 | B2 | 5/2013 | Leroy et al. |
| 8,447,384 | B2 | 5/2013 | Xu et al. |
| 8,452,613 | B2 | 5/2013 | Meinel et al. |
| 8,437,527 | B2 | 7/2013 | Kasahara |
| 2003/0128801 | A1 | 7/2003 | Eisenberg et al. |
| 2003/0194050 | A1 | 10/2003 | Eberhard et al. |
| 2004/0066909 | A1 | 4/2004 | Lonn et al. |
| 2004/0210133 | A1 | 10/2004 | Nir |
| 2005/0027187 | A1 | 2/2005 | Barth et al. |
| 2005/0049502 | A1 | 3/2005 | Schoisswohl |
| 2005/0249398 | A1 | 11/2005 | Khamene et al. |
| 2006/0002630 | A1 | 1/2006 | Fu et al. |
| 2007/0270687 | A1 | 11/2007 | Gardi et al. |
| 2008/0009699 | A1 | 1/2008 | Sakas et al. |
| 2008/0064949 | A1 | 3/2008 | Hertel et al. |
| 2010/0036247 | A1 | 11/2010 | Yamamoto et al. |
| 2011/0081063 | A1 | 4/2011 | Leroy et al. |
| 2011/0238043 | A1 | 9/2011 | Kleven |
| 2012/0071749 | A1 | 3/2012 | Xu et al. |
| 2012/0245455 | A1 | 9/2012 | Bauman et al. |
| 2013/0172739 | A1 | 4/2013 | Paladini |
| 2013/0121457 | A1* | 5/2013 | Maltz .................. A61B 6/032 378/4 |
| 2013/0170721 | A1* | 7/2013 | Kim ..................... G06K 9/40 382/131 |
| 2014/0050375 | A1* | 2/2014 | Baker ................ G06F 19/3481 382/128 |

OTHER PUBLICATIONS

BioJet 4D Prostate Image Fusion Technology, Brochure, 2013, pp. 1-4, Geo Scan Medical, Lakewood Ranch, FL, US.

UroNav Fusion Biopsy System, Brochure, 2013, pp. 1-3, Invivo Corp., Florida, US.

MRI-Ultrasound Fusion Permits Targeted Biopsy for Prostate Cancer, Brochure, 2013, pp. 1-3, 13v2-04:03-13, UCLA Health, California, US.

Weiss, Seitz, et al., MR-US Fusion for Targeted Prostate Biopsy, International Society for Magnetic Resonance in Medicine (ISMRM) Conference, Stockholm, Sweden, May 2010.

Lindseth, Kaspersen, et al., Multimodal Image Fusion in Ultrasound-Based Neuronavigation: Improving Overview and Interpretation by Integrating Preoperative MRI with Intraoperative 3D Ultrasound, 2003, CAS Journal, Trondheim, Norway.

Sonowand Invite, Brochure, 2012, pp. 1-7, Sonowand AS, Trondheim, Norway.

Marks, Ward, et al., Tracking of prostate biopsy sites using a 3D Ultrasound device (Artemis), Symposium, May 2010, American Urological Association, San Francisco, California, US.

Natarajan, Marks, et al., Clinical application of a 3D ultrasound-guided prostate biopsy system, Urologic Oncology: Seminars and Original Investigations 29 (2011) 334-342, UCLA, CA, USA.

International Search Report fort PCT/US2013/072154 published as WO 2015/080716 A1.

\* cited by examiner

MULTI-IMAGING MODALITY NAVIGATION SYSTEM

RELATED APPLICATION

This application is a national filing of PCT application Serial No. PCT/US2013/072154, filed Nov. 27, 2013, published as WO2015/080716 on Apr. 6, 2015. This application claims priority to PCT application Serial No. PCT/US2013/072154, published as WO2015/080716 on Apr. 6, 2015.

TECHNICAL FIELD

The following generally relates to imaging and finds particular application to a multi-imaging modality navigation system.

BACKGROUND

An ultrasound imaging system includes a transducer array that transmits an ultrasound beam into an examination field of view. As the beam traverses structure (e.g., of a sub-portion of an object or subject) in the field of view, sub-portions of the beam are attenuated, scattered, and/or reflected off the structure, with some of the reflections (echoes) traversing back towards the transducer array. The transducer array receives echoes, which are processed to generate an image of the sub-portion of the object or subject. The image is visually displayed.

Ultrasound imaging is used in a wide range of medical and non-medical applications. An example of a medical application is ultrasound guided biopsy. Generally, a biopsy is a procedure in which a small sample(s) of tissue of interest (e.g., prostate, lung, breast, etc.) is removed for subsequent examination for abnormalities such as cancer cells. For a biopsy, a needle is inserted through the skin and advanced to the target tissue where the sample(s) is taken. A biopsy typically is performed in response to finding a lump, abnormal physical enlargement of tissue, etc.

With ultrasound guided biopsy, ultrasound is used to assist a clinician with locating and/or navigating the needle to the tissue of interest. A non-limiting approach is described in Pelissier et al., Ser. No. 12/775,403, filed May 6, 2010, and entitled "Freehand Ultrasound Imaging Systems and Method for Guiding Find Elongate Instruments," which is incorporated herein by reference in its entirety. In '403, electro-magnetic sensors are affixed to both the ultrasound probe and a needle instrument, and communicate with a position tracking system, which monitors the position and orientation thereof.

In '403, the transducer probe is placed against the patient and 2D data is acquired. The location of the probe (and the needle where the needle instrument is affixed to the probe), relative to the ultrasound image, is determined from the tracking sensors on the probe. In '403, where the needle instrument is not affixed to the probe, once the target tissue is located, the location of the needle, relative to the ultrasound image, is determined from the tracking sensors on the needle instrument. Both scenarios allow the clinician to determine the location of the probe and/or the needle in 3D space.

With another approach, structural 3D volumetric image data from a second modality is also used for guidance. MRI systems, generally, are capable of capturing high resolution, 3D data that is rich in internal structure and features. Ultrasound, in comparison, is capable of capturing low to medium-high resolution data sets, both two-dimensional and three-dimensional, at high acquisition rates that can support real-time interaction. For this approach, the 3D MRI image data is acquired before the biopsy. Then, during the biopsy, the 2D ultrasound data is fused with the 3D MRI data.

This has included segmentation to delineate different tissue types followed by registration of the 2D US data and the 3D MRI data. The scale and structure of the data sets produced by these two modalities is generally very different due to the different physical information captured by the modalities, requiring an initial "normalization" procedure to remap one or both of the data sets to bring them as closely as possible into structurally comparable spaces. The fused data and the tracking system are used to guide the probe to the target tissue, which is identified from the structural image data.

Unfortunately, electro-mechanical sensor based tracking systems often require expensive equipment and manual procedures in order to extract critical information concerning the presence and extent of malignancies. Even the latest ultrasound and MRI fusion-based systems require expensive hardware-based tracking technology. Furthermore, currently, the clinician will take more samples than is absolutely necessary, in both target tissues and surrounding tissue due to uncertainty in both correlation and tracking. This may lead to increased procedure time and patient discomfort.

SUMMARY

Aspects of the application address the above matters, and others.

In one aspect, a method includes obtaining first 3D imaging data for a volume of interest. The first 3D imaging data includes structural imaging data and a target tissue of interest. The method further includes obtaining 2D imaging data. The 2D imaging data includes structural imaging data for a plane of the volume of interest. The plane includes at least three fiducial markers of a set of fiducial markers. The method further includes locating a plane, including location and orientation, in the first 3D imaging data that corresponds to the plane of the 2D imaging data by matching the at least three fiducial markers with corresponding fiducial markers identified in the first 3D imaging data and using the map. The method further includes visually displaying the first 3D imaging data with the 2D imaging data superimposed over at the corresponding plane located in the first 3D imaging data.

In another aspect, a multi-modality navigation system includes an imaging data processor that processes at least one of 3D volumetric non-US imaging data or 3D volumetric US imaging data, producing at least one of first and second image data in which structure represented in the at least one of 3D volumetric non-US imaging data and the 3D volumetric US imaging data is visually enhanced. The multi-modality navigation system further includes a 3D US imaging data to 3D non-US imaging data mapping generator that fuses the processed at least one of the 3D volumetric non-US imaging data and the 3D volumetric US imaging data and generates a mapping there between based on the fused processed at least one of the 3D volumetric non-US imaging data and the 3D volumetric US imaging data. The mapping further maps markers identified in the 3D volumetric non-US imaging data to the 3D US imaging data. The mapping further maps target tissue identified in the 3D volumetric non-US imaging data to the 3D US imaging data. The multi-modality navigation system further includes a 2D US imaging data to 3D non-US imaging data combiner that combines 2D US imaging data with the 3D non-US imaging data. The combiner places the 2D US imaging data at a location and orientation in the 3D non-US imaging data corresponding to a same plane based on the mapping and the markers. The multi-modality navigation system further includes a display that concurrently displays the combined 3D non-US imaging data and the 2D US imaging data.

In another aspect, a computer readable storage medium is encoded with computer executable instructions, which, when executed by a processor, causes the processor to: track a location of an US probe with respect to non-US 3D imaging data based on a mapping between a US 3D imaging data and the non-US 3D imaging and a set of fiducials representing structure visually present in both the US 3D imaging data and the non-US 3D imaging and current US 2D imaging data. The computer executable instructions, when executed by the processor, further cause the processor to: suggest a path for the US probe from a current location of the US probe to target tissue of interest based at least on the mapping.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

The following describes an approach for tracking a location of an US imaging probe with respect to a volume of interest during an imaging procedure using on 2D imaging data acquired with the US imaging probe and previously acquired 3D imaging data of the volume of interest based on a set of fiducial markers that are visually present in both the 2D imaging data and the 3D imaging data. The following also describes an approach for suggesting movement of the probe to move the probe such that target tissue of interest is in the field of view of the probe.

This approach, for example, facilitates locating target tissue(s) of interest in connection with applications such as a biopsy of the prostate gland. In one instance, the tracking and/or movement is achieved without use of any external tracking system (e.g., electro-mechanical sensors) and/or segmentation of tissue from in the 2D imaging data and/or the 3D imaging data. As such, the approach described herein can mitigate hardware-based tracking, provide superior and faster location identification, and reduce overall procedure cost and procedure time.

Figure 1:
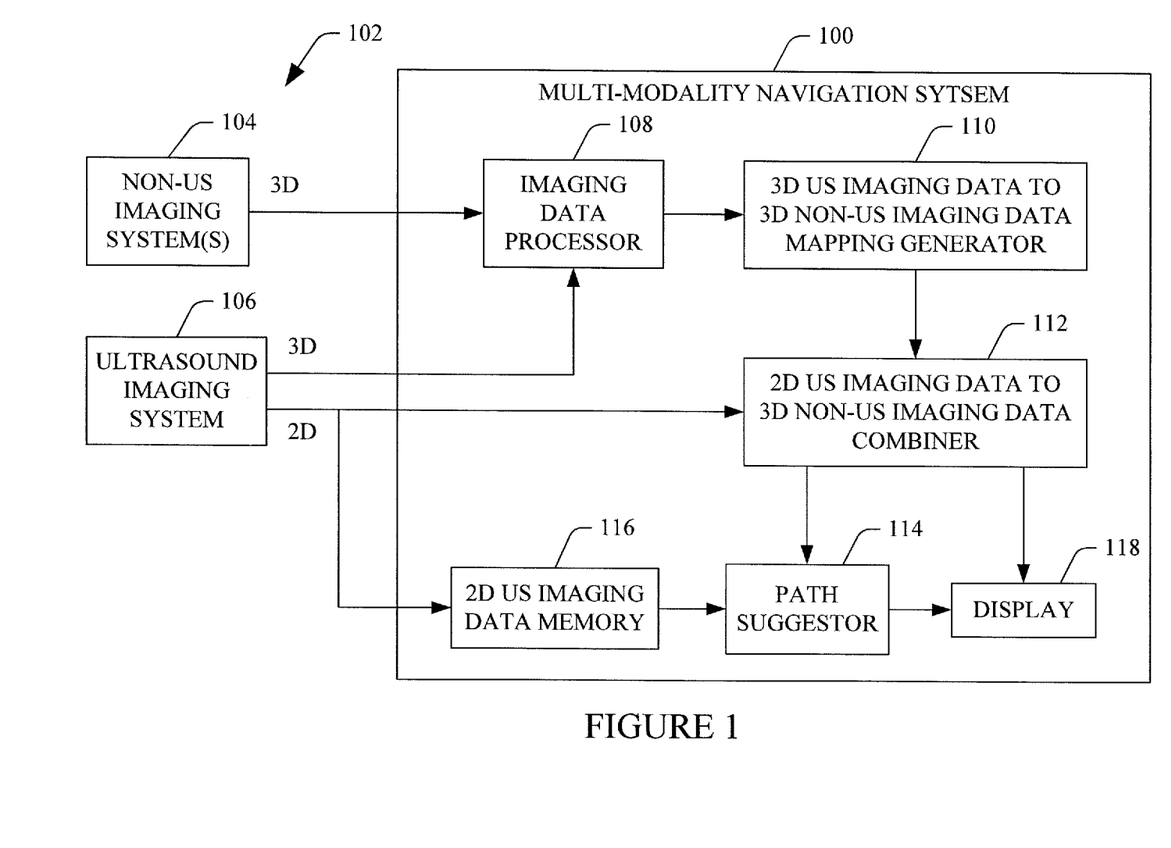
FIG. 1 schematically illustrates an example multi-modality navigation system.

FIG. 1 schematically illustrates an example multi-modality navigation system 100 in connection with two or more imaging systems 102. The illustrated multi-modality navigation system 100 receives imaging data from the two or more imaging systems 102. In the illustrated example, the two or more imaging systems 102 include at least one non-US imaging system 104 and an US imaging system 106.

The at least one non-US imaging system 104 generates 3D structural imaging data. As utilized herein, the term "structural imaging data" refers to imaging data that includes voxels with values that correspond to scanned structure such as, for example, organs, bone, tumor, etc., as opposed to functional imaging data in which the voxels are indicative of function such as, for example, changes in metabolism, agent uptake/washout, etc.

The non-US imaging system 104 is, e.g., an MRI imaging system, a CT imaging system, etc. In a variation, the non-US 3D imaging data is obtained from a data repository such as a radiology information system (RIS), a hospital information system (HIS), an electronic medical record (EMR), and/or other data repository. Further, the non-US 3D imaging data may include 3D imaging data from more than one imaging system.

The US imaging system 106 generates 3D and 2D structural US imaging data. The US imaging data, generally, will have lower resolution than the non-US imaging data. The US imaging system 106 is employed during a procedure to generate initial 3D imaging data and then subsequent 2D imaging data or subsequent 2D imaging data and subsequent 3D imaging data. For the latter, e.g., this may include generating 3D US imaging data after a predetermined number of 2D US imaging data frames. With a prostate biopsy procedure, 2D US imaging data is acquired at fixed time intervals (e.g., a fraction of a second), as the user guides the probe to the target locations for sampling.

The multi-modality navigation system 100 includes an imaging data processor 108. The imaging data processor 108 processes the non-US 3D imaging data and/or the US 3D imaging data. As described in greater detail below, in one instance, such processing includes visually enhancing anatomical structure represented in both the non-US 3D imaging data and/or the US 3D imaging data, rendering image data sets that are more similar, structurally, than before the processing.

The multi-modality navigation system 100 further includes a 3D US imaging data to 3D non-US imaging data mapping generator 110. The 3D US imaging data to 3D non-US imaging data mapping generator 110 generates a mapping between the 3D US imaging data and the 3D non-US imaging data. As described in greater detail below, the mapping is based on the enhanced structure and an initial set of fiducial markers identified in the 3D non-US imaging data. The fiducial markers may include an anatomical fiducial marker, a tissue fiducial marker, and/or fiducial marker.

The mapping allows one or more target tissues identified in the 3D non-US imaging data to be located in the 3D US imaging data. The mapping also allows the initial set of fiducial markers to be located in the 3D US imaging data. Once mapped, one or more additional fiducial markers, corresponding to structure visually present in both types of imaging data (in low, mid and high resolution) can be identified. The initial and/or additional fiducial markers are manually or semi-automatically identified.

The multi-modality navigation system 100 further includes a 2D US imaging data to 3D non-US imaging data combiner 112. The combiner 112 combines current 2D US imaging data with the non-US 3D imaging data. As described in greater detail below, this includes matching the fiducial markers of the 2D US imaging data with the fiducial markers in the non-US 3D imaging data, which matches the current 2D US imaging data to the plane and orientation in the non-US 3D imaging data.

The multi-modality navigation system 100 further includes a path suggestor 114 that suggests a path from the current location of the US probe that will place the US probe at a target tissue (or other identified tissue) location at which the target tissue will be in the field of view of the US probe. The path is suggested based on 2D US imaging data acquired during one or more acquisition frames (store in memory 116), e.g., from information such as velocity, acceleration, direction, etc. of the US probe there between is derived.

The multi-modality navigation system 100 further includes a display 118. In one instance, the 3D non-US imaging data is displayed with the current 2D US image data superimposed there over. This allows the user to visually see where the US probe is currently located relative to the target tissue(s) of interest identified in the non-US imaging data. Alphanumeric and/or graphical indicia is concurrently rendered to visually show the suggested path, including predicted direction, translation and/or rotation of the probe to position the probe so that a target tissue is in the field of view.

The multi-modality navigation system 100 allows for tracking the location of the US probe with respect to the target tissue(s) and the 3D non-US imaging data via software, without any electro-mechanical tracking sensors affixed to the US probe. Additionally, the image data processing and fiducial markers mitigate a need for segmenting the target tissue(s) into discernible blobs or tissue and registering the blobs. Furthermore, the multi-modality navigation system 100 allows for predicting a path for the US probe to the target tissue(s) with higher confidence in less time.

It is to be appreciated that the multi-modality navigation system 100 can be implemented via one or more computer processors (e.g., a central processing unit (CPU), a microprocessor, a controller, etc.) executing one or more computer executable instructions embedded or encoded on computer readable storage medium, which excludes transitory medium, such as physical memory. However, at least one of the computer executable instructions can alternatively be carried by a carrier wave, signal, and other transitory medium and implemented via the one or more computer processors.

Figure 2:
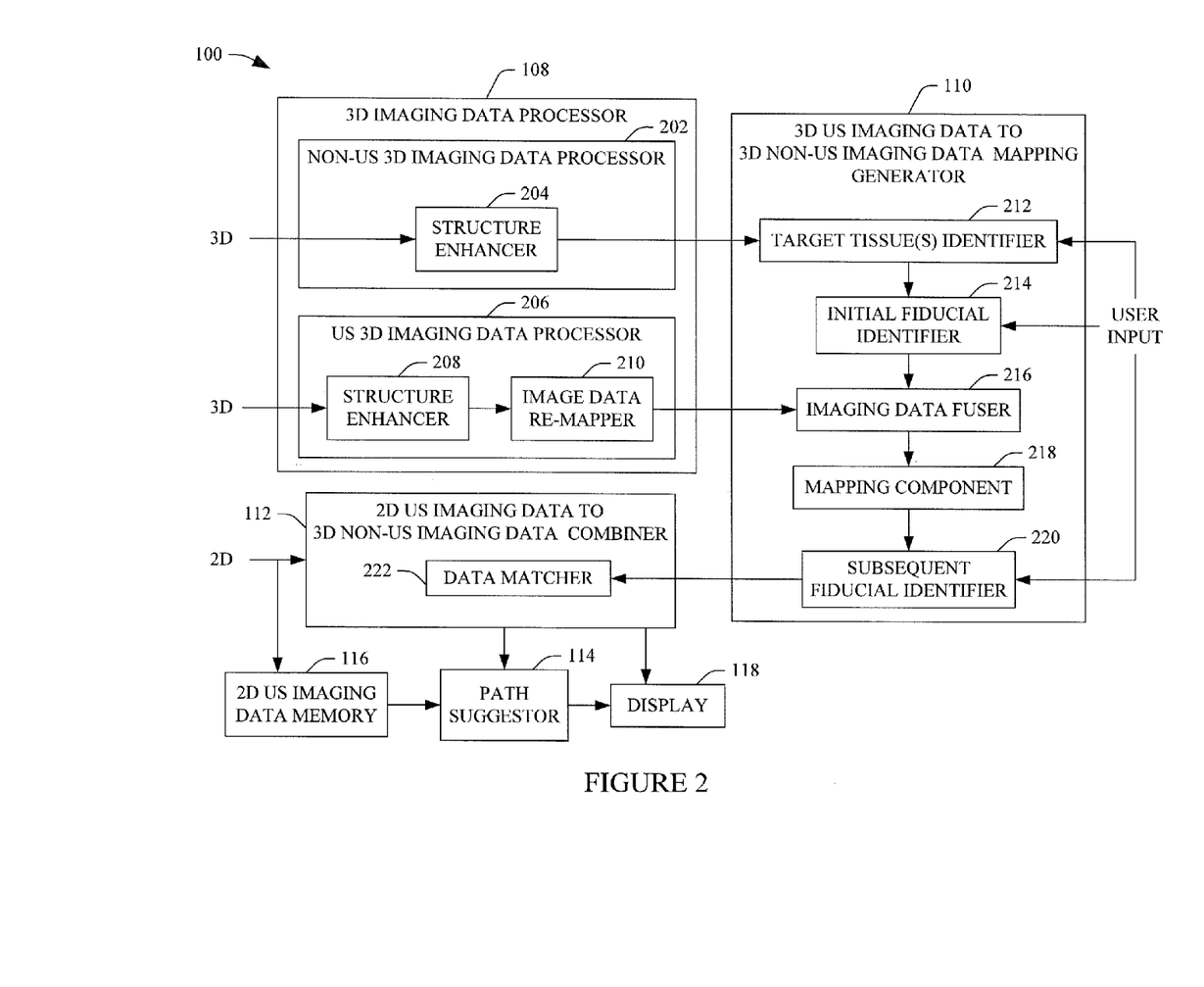
FIG. 2 schematically illustrates an example imaging data processor, a 3D US imaging data to 3D non-US imaging data mapping generator, and a 2D US imaging data to 3D non-US imaging data combiner of the multi-modality navigation system of FIG. 1.

FIG. 2 schematically illustrates an example of the 3D imaging data processor 108, the 3D US imaging data to 3D non-US imaging data mapping generator 110, and the 2D US imaging data to 3D non-US imaging data combiner 112. As discussed herein, the 3D imaging data processor 108 processes the 3D non-US imaging data and/or the 3D US imaging data. In this example, the 3D imaging data processor 108 processes both the 3D non-US imaging data and the 3D US imaging data.

The 3D imaging data processor 108 includes a non-US 3D imaging data processor 202. The non-US 3D imaging data processor 202 includes a structure enhancer 204. The structure enhancer 204 visually enhances certain structural characteristics such as edges of tissue, boundaries between tissue, boundaries between structure such as tissue, etc. This can be achieved, for example, by applying a gradient operator, scaling the amplitude of the voxels values, etc. The non-US 3D imaging data processor 102 can include additional or alternative processing components.

The 3D imaging data processor 108 also includes a US 3D imaging data processor 206. The US 3D imaging data processor 206 includes a structure enhancer 208 and an image data re-mapper 210. The structure enhancer 208 visually enhances certain structural characteristics such as edges of tissue, boundaries between tissue, etc., for example, by removing speckle, applying a gradient operator, scaling the amplitude of the voxels values, etc.

The image data re-mapper 210 scales the US 3D imaging data to that of a size of the non-US 3D imaging data and scales the amplitude so that a total amplitude of each of the non-US 3D imaging data and the US 3D imaging data is approximately a same amplitude. Similar to the non-US 3D imaging data processor 202, the US 3D imaging data processor 206 can include additional or alternative processing components.

By way of example, in one instance, the US 3D imaging data processor 206 enhances structure in the US 3D imaging data by de-speckling the US 3D imaging data, applying a gradient to find the edges of tissue, re-scaling the US 3D imaging data and/or the non-US 3D imaging data (e.g., so that the size of the US 3D imaging data and the size of the non-US 3D imaging data are approximately the same, and re-scaling an intensity of the US 3D imaging data and/or the non-US 3D imaging data (e.g., so that a total intensity of the non-US 3D imaging data and an intensity of the non-US 3D imaging data match). Such processing transforms the US 3D imaging data to a 3D frame of reference that is more similar to that of the non-US 3D imaging data.

The 3D US imaging data to 3D non-US imaging data mapping generator 110 includes a target tissue identifier 212. The target tissue identifier 212 allows a user to identify target tissue(s) of interest in the non-US 3D imaging data. This may include providing the user with tools that allow the user to manually trace the target tissue, set a seed point in the target tissue and then invoke automatic extraction, select the tissue by name and invoke automatic extraction, etc.

The 3D US imaging data to 3D non-US imaging data mapping generator 110 further includes an initial fiducial identifier 214 that identifies the initial set of fiducial markers in the non-US 3D imaging data. One of more of the fiducial markers can be set manually by the user via the user input. Additionally or alternatively, one of more of the fiducial markers can be set automatically and changed, confirmed and/or rejected by the user via the user input.

The 3D US imaging data to 3D non-US imaging data mapping generator 110 further includes an imaging data fuser 216. The imaging data fuser 216 fuses the non-US 3D imaging data and the US 3D imaging data together.

The 3D US imaging data to 3D non-US imaging data mapping generator 110 further includes a mapping component 218. The mapping component 218 generates a map or mapping between the fused non-US 3D imaging data and the US 3D imaging data based on the enhanced structure and the initial set of fiducial markers. The map allows any location in the US 3D imaging data to be mapped to the non-US 3D imaging data. The map further allows the target tissue and/or one or more fiducial markers to be located in the US 3D imaging data.

The 3D US imaging data to 3D non-US imaging data mapping generator 110 further includes a subsequent fiducial identifier 220. The subsequent fiducial identifier 220 allows a user to identify one or more additional fiducial markers. Likewise, the one or more of the fiducial markers can be set manually by the user via the user input and/or automatically and changed, confirmed and/or rejected by the user via the user input.

The 2D US imaging data to non-US 3D imaging data combiner 112 includes a data matcher 222. The data matcher 222 matches current 2D US imaging data to the non-US 3D imaging data based on the fiducial markers. The current 2D US imaging data is acquired so that it includes at least three of the fiducial markers. The data matcher 222 maps the location and orientation of the 2D US imaging data to a plane of the non-US 3D imaging data based on the at least three fiducial markers.

Generally, at least three co-planar fiducial markers are used to match the 2D US imaging data with a plane in the 3D non-US imaging data. However, more than three co-planar anatomical fiducial markers can be used. Using more than three co-planar anatomical fiducial markers may mitigate error due to tissue deformation, which may move a fiducial marker in the 2D US imaging data so that it is no longer in alignment with the corresponding fiducial marker in the 3D non-US imaging data.

Using more than three co-planar fiducial markers may also improve the resolution of the fit. The additional fiducial markers may also be co-planar. However, a fiducial marker that is in the 3D non-US imaging data but out of plane with respect to the 2D US imaging data can also be used. At least squares or other approach can be used to fit the 2D US imaging data to the 3D non-US imaging data. The fit, in one instance, optimizes a correlation between the imaging data sets.

Where 3D US imaging data is acquired, the 2D US imaging data to non-US 3D imaging data combiner 112 employs a similar approach to mapping the 3D US imaging data to a corresponding location and orientation in the 3D non-US imaging data. The 3D non-US imaging data is concurrently displayed with the 2D US imaging data at the determined location and orientation in the non-US 3D imaging data. A suggested path is determined as described herein and concurrently displayed.

Figure 3:
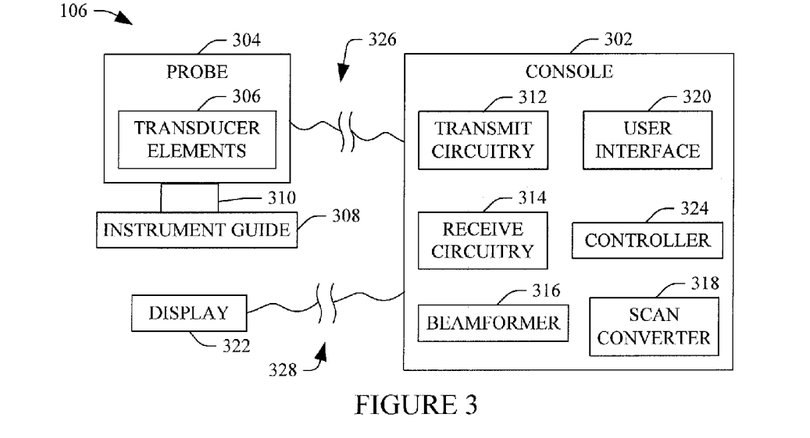
FIG. 3 schematically illustrates an example US imaging system with an instrument navigation guide affixed to an US probe thereof.

FIG. 3 illustrates an example of the US imaging system 106. In this example, the US imaging system 106 includes a console 302 and a separate US transducer probe 304 that interfaces therewith.

The ultrasound transducer probe 304 includes a transducer array with a plurality of transducer elements 306. The transducer array can be linear, curved, and/or otherwise shaped, fully populated, sparse and/or a combination thereof, etc. The transducer elements 306 can be operated in 2D and/or 3D mode. The transducer elements 306 transmit ultrasound signals and receive echo signals.

An instrument guide 308, such as a biopsy needle guide, is affixed to the US transducer probe 304 through a coupling 310 such as a bracket, clamp, etc. In one instance, the biopsy needle is supported in the instrument guide 308 in a retracted position until a target tissue of interest is located with the US transducer probe 304 as described herein. Then, the needle is advanced to acquire the sample of the target tissue of interest.

Transmit circuitry 312 selectively actuates or excites one or more of the transducer elements 306. More particularly, the transmit circuitry 312 generates a set of pulses (or a pulsed signal) that are conveyed to the transducer elements 306. The set of pulses actuates a set of the transducer elements 306, causing the transducer elements 306 to transmit ultrasound signals into an examination or scan field of view.

Receive circuitry 314 receives a set of echoes (or echo signals) generated in response to the transmitted ultrasound signals. The echoes, generally, are a result of the interaction between the emitted ultrasound signals and the object (e.g., flowing blood cells, organ cells, etc.) in the scan field of view. The receive circuit 314 may be configured for spatial compounding, filtering (e.g., FIR and/or IIR), and/or other echo processing.

A beamformer 316 processes the received echoes. In B-mode, this includes applying time delays and weights to the echoes and summing the delayed and weighted echoes. A scan converter 318 scan converts the data for display, e.g., by converting the beamformed data to the coordinate system of a display or display region used to visually present the resulting data.

A user interface (UI) 320 include one or more input devices (e.g., a button, a knob, a slider, etc., touchscreen and/or physical mechanical device) and/or one or more output devices (e.g., a liquid crystal display, a light emitting diode, etc.), which allows for interaction between with the system 106. A display 322 visually displays the US imaging data.

A controller 324 controls the various components of the system 106. For example, such control may include actuating or exciting individual or groups of transducer elements of the transducer array 202 for an A-mode, B-mode, C-plane, and/or other data acquisition mode, steering and/or focusing the transmitted signal, etc., actuating the transducer elements 306 for steering and/or focusing the received echoes, etc.

The US probe 304 and the display 322 are physically separate electromechanical components with respect to the console 302. The US probe 304 and the display 322 communicate with the console 302 through communications paths 326 and 328. The communications paths 326 and 328 can be wired (e.g., a physical cable and connectors) and/or wireless.

Figure 4:
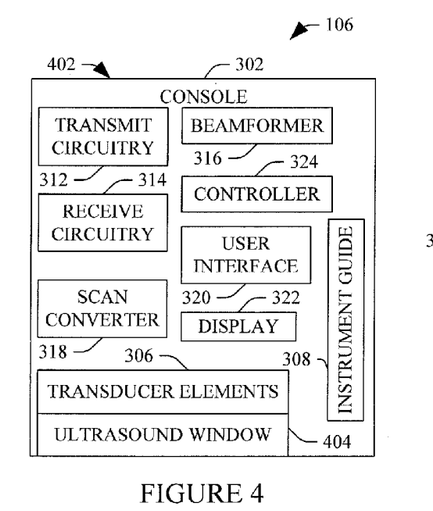
FIG. 4 schematically illustrates an example hand-held US imaging system with an instrument navigation guide affixed externally thereto.

FIG. 4 illustrates a variation of the US imaging system 106. In this example, the console 302 includes a single housing 402. The single housing 402 houses and physically supports the transducer elements 306, the instrument guide 308, the transmit circuitry 312, the receive circuitry 314, the beamformer 316, the scan converter 318 and the controller 324, all of which are inside the single housing 402.

The user interface 320 and/or the display 322 are part of the housing 402. For example, the display 322, in one instance, is a sub-portion of one of the sides of the housing 402. The user interface 320 may include physical mechanical controls at other locations of the housing 402. An ultrasound window 404 is also part of or integrated with the console 200. In this instance, the transducer elements 204 are disposed in the housing 402 behind the ultrasound window 404 and emit signals and receive echoes there through.

In FIG. 4, the US imaging system 106 is a hand-held ultrasound apparatus, which uses internally located power, e.g., from a power source such as a battery, a capacitor, etc. to power the components therein, and/or power from an external power source. An example of a hand-held device are described in U.S. Pat. No. 7,699,776 to Walker et al., entitled "Intuitive Ultrasonic Imaging System and Related Method Thereof," and filed on Mar. 6, 2003, which is incorporated herein in its entirety by reference.

An example of hand-held ultrasound apparatus with an internal instrument guide is described in Ser. No. 13/017,344 to O'Conner, entitled "Ultrasound imaging apparatus," and filed on Jan. 31, 2011, and an example with an external instrument guide is described in U.S. Pat. No. 8,226,562 to Pelissier, entitled "Hand-Held Ultrasound System Having Sterile Enclosure," and filed on Aug. 7, 208, both of which are incorporated herein in their entirety by reference.

Figure 5:
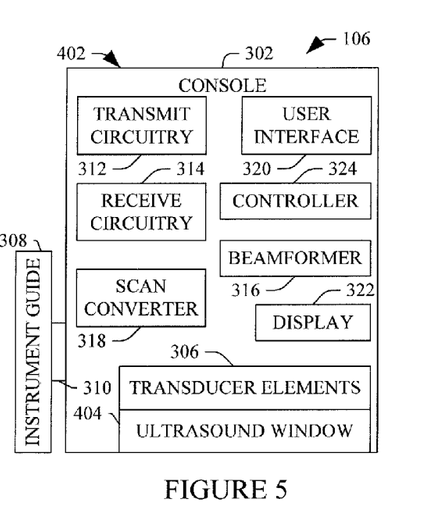
FIG. 5 schematically illustrates example hand-held US imaging system with an instrument navigation guide integrated therein.

FIG. 5 illustrates a variation of FIG. 4 in which the instrument guide 308 is disposed out of the single housing 402 and affixed thereto through the coupling 310.

Although the approach described herein does not require the user of an external tracking system and/or electro-mechanical sensors, an external tracking system and/or electro-mechanical sensors can be used with the approach described herein. For example, where the instrument guide is not part of the imaging system 106 or affixed thereto, electro-mechanical sensors affixed to the instrument can be registered to the 3D non-US imaging data coordinate system and used to the track the instrument.

Figure 6:
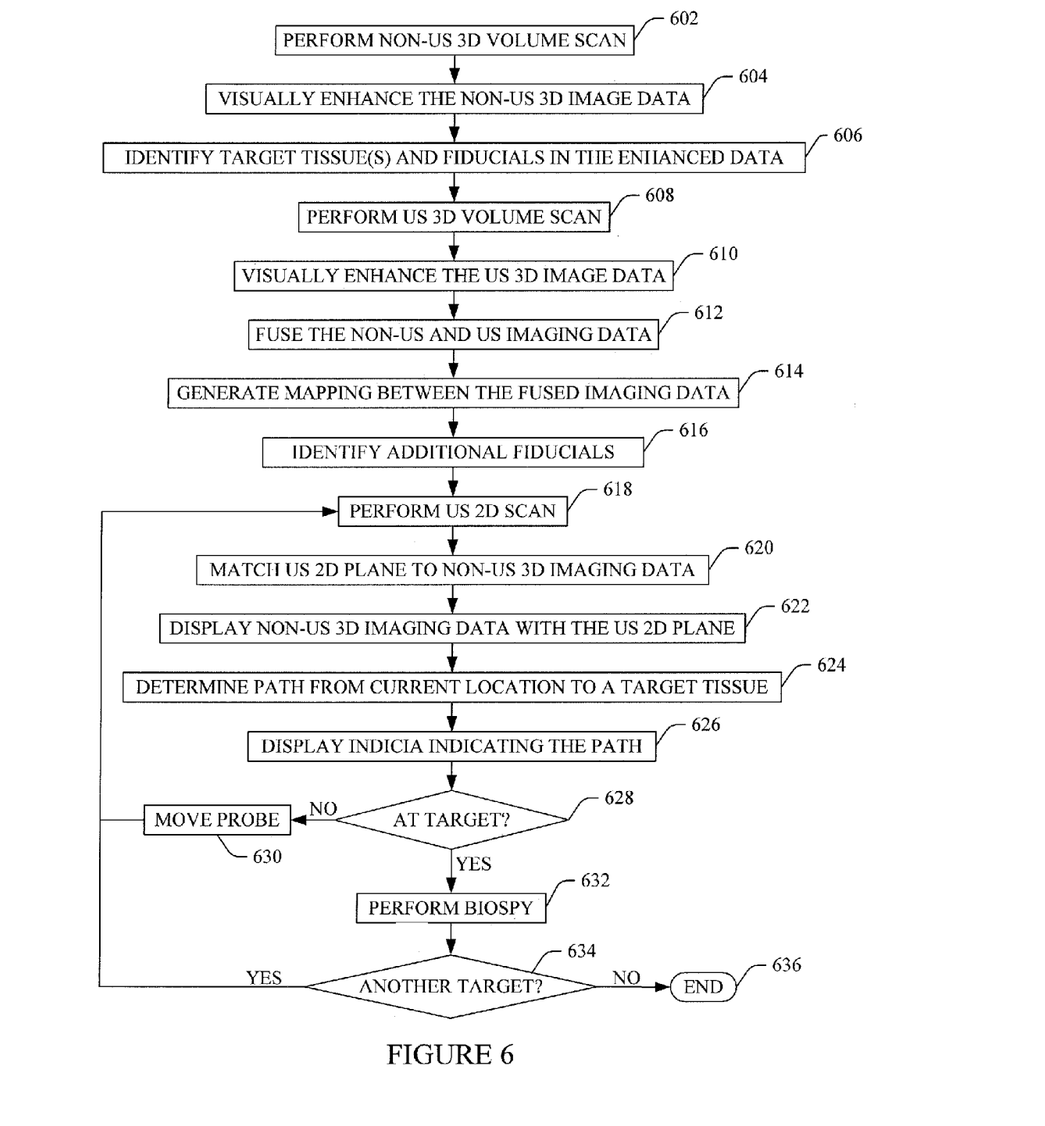
FIG. 6 illustrates an example method for multi-modality navigation.

FIG. 6 illustrates a method for navigating a US probe to a target tissue of interest.

Note that the ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 602, a 3D volumetric structural scan of a volume of interest is performed, generating 3D volumetric structural imaging data.

At 604, the 3D volumetric structural imaging data is processed to visually enhance structural (e.g., edges, boundaries, etc.) represented therein.

At 606, one or more target tissues of interest and an initial set of fiducial markers are identified in the visually enhanced 3D volumetric structural imaging data.

At 608, a 3D volumetric US scan of the volume of interest is performed, generating 3D volumetric US imaging data.

At 610, the 3D US volumetric structural imaging data is processed to visually enhance structural (e.g., edges, boundaries, etc.) represented therein.

At 612, the visually enhanced non-US and US volumetric structural imaging data are fused.

At 614, a mapping between the fused visually enhanced non-US and US volumetric structural imaging data is generated.

At 616, additional fiducial markers are identified in the 3D non-US imaging data of the fused imaging data.

At 618, a 2D US scan of a plane of the volume is performed with of a US probe, generating 2D US imaging data. As discussed herein, the scanned plane includes at least three co-planar fiducial makers.

At 620, the 2D US plane is matched to a corresponding 2D plane in the 3D volumetric structural imaging data based on the fiducial markers.

At 622, the 3D volumetric structural imaging data is displayed with the 2D US plane superimposed thereover at the location of the corresponding 2D plane.

At 624, a path from the current location of the US probe to the target tissue is determined based on previously performed 2D US scan during the procedure.

At 626, indicia indicating the path is concurrently superimposed over the displayed the 3D volumetric structural imaging data.

At 628, it is determined if the target tissue is in the field of view of the US probe.

If the target tissue is not in the field of view of the US probe, then at 630, the US probe is moved based on the suggested path, and acts 618 to 628 are repeated.

If the target tissue is in the field of view of the US probe, then at 632, the target tissue is biopsied.

At 634, it is determined if there is other target tissue to biopsy.

If there is other target tissue to biopsy, then acts 618 to 632 are repeated.

If there is no further target tissue to biopsy, then at 636, the procedure is completed and/or no longer uses the multi-imaging modality navigation system 100.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
obtaining first 3D imaging data for a volume of interest, wherein the first 3D imaging data includes structural imaging data and a target tissue of interest;
obtaining 2D imaging data, wherein the 2D imaging data includes structural imaging data represented in the volume of interest, wherein the 2D imaging data includes at least three anatomical or tissue fiducial markers of a set of anatomical or tissue fiducial markers;
locating a plane, including location and orientation, in the first 3D imaging data that corresponds to the plane of the 2D imaging data by matching, using a predetermined map, the at least three anatomical or tissue fiducial markers in the 2D imaging data with corresponding anatomical or tissue fiducial markers identified in the first 3D imaging data; and
visually displaying the first 3D imaging data with the 2D imaging data superimposed over at the corresponding plane located in the first 3D imaging data.

2. The method of claim 1, further comprising:
obtaining second 3D imaging data for the volume of interest, wherein the second 3D imaging data includes structural imaging data and the target tissue of interest, wherein the first and second imaging data correspond to different imaging modalities; and
generating the predetermined map between voxels of the first 3D imaging data and the second 3D imaging data by fusing the first 3D imaging data and the second 3D imaging data and based on the set of anatomical or tissue fiducial markers identified in the first 3D imaging data, wherein the map provides a mapping of the set of anatomical or tissue fiducial markers and the target tissue to corresponding locations in the second 3D imaging data.

3. The method of claim 2, wherein the at least three anatomical or tissue fiducial markers include an anatomical structure that is visually present in both the first 3D imaging data and the second 3D imaging data.

4. The method of claim 3, wherein the anatomical structure includes an edge of tissue or a boundary between two different tissues.

5. The method of claim 1, further comprising:
visually enhancing structure in the first 3D imaging data;
identifying the target tissue in the visually enhanced first 3D imaging data; and
identifying the set of anatomical fiducial markers in the visually enhanced first 3D imaging data.

6. The method of claim 5, wherein the structure is visually enhanced by applying one or more of a gradient or amplitude scaling.

7. The method of claim 4, further comprising:
visually enhancing structure in the second 3D imaging data.

8. The method of claim 7, wherein the structure is visually enhanced by removing speckling from the second 3D imaging data.

9. The method of claim 7, further comprising:
scaling a size of at least one of the first 3D imaging data or the second 3D imaging data to be approximately equal to a size of at least one of the second 3D imaging data or the first 3D imaging data.

10. The method of claim 7, further comprising:
scaling an intensity value of each voxel of the first 3D imaging data and of the second 3D imaging data so that a total intensity of the first 3D imaging data and of the second 3D imaging data is approximately equal.

11. The method of claim 1, wherein the 2D imaging data is acquired with an US probe, which has a field of view, and further comprising:
determining a path for the US probe that is predicted to move the US probe from a current location in the first 3D imaging data to a location in which the target tissue is in the field of view of the US probe, wherein the path is based on 2D imaging data acquired in a predetermined number of acquisition frames prior to acquisition of the 2D imaging data.

12. The method of claim 11, wherein the path is based on one or more of a velocity or an acceleration of movement of the US probe between the frames.

13. The method of claim 11, further comprising:
visually displaying indicia showing the path superimposed over the displayed first 3D imaging data, wherein the indicia shows predicated translation and rotation.

14. The method of claim 2, wherein the first 3D imaging data has first image resolution and the second 3D imaging data has second image resolution, and the first image resolution is greater than the second image resolution.

15. The method of claim 2, wherein the first 3D imaging data is generated with a first imaging modality and the second 3D imaging data is generated with a second imaging modality, wherein the first imaging modality is one of MRI or CT and second imaging modality is US.

16. A multi-modality navigation system, comprising:
an imaging data processor that processes at least one of 3D volumetric non-US imaging data or 3D volumetric US imaging data, respectively producing at least one of first or second image data in which structure represented in the at least one of 3D volumetric non-US imaging data or the 3D volumetric US imaging data is visually enhanced;
a 3D US imaging data to 3D non-US imaging data mapping generator that fuses the processed at least one of the 3D volumetric non-US imaging data and the 3D volumetric US imaging data and the other of the 3D volumetric non-US imaging data and the 3D volumetric US imaging data and generates a mapping between the processed at least one of the 3D volumetric non-US imaging data and the 3D volumetric US imaging data and the other of the 3D volumetric non-US imaging data and the 3D volumetric US imaging data based on the fused processed at least one of the 3D volumetric non-US imaging data and the 3D volumetric US imaging data, wherein the mapping further maps anatomical or tissue markers identified in the 3D volumetric non-US imaging data to the 3D US imaging data, and wherein the mapping further maps target tissue identified in the 3D volumetric non-US imaging data to the 3D US imaging data;
a 2D US imaging data to 3D non-US imaging data combiner that combines 2D US imaging data with the 3D non-US imaging data, wherein the combiner places the 2D US imaging data at a location and orientation in the 3D non-US imaging data corresponding to a same plane based on the mapping and the anatomical or tissue markers; and
a display that concurrently displays the combined 3D non-US imaging data and the 2D US imaging data.

17. The multi-modality navigation system of claim 16, further comprising:
a path suggestor that suggest a path for a US probe that acquired the 2D US imaging data, wherein the suggested path predicts a path from a current location of the US probe to a location of tissue of interest.

18. The multi-modality navigation system of claim 16, wherein the 3D non-US imaging data includes at least one of MRI 3D imaging data or CT 3D imaging data.

19. The multi-modality navigation system of claim 16, wherein the imaging data processor processes the 3D volumetric non-US imaging data by applying at least one of an edge detection or an amplitude scaling algorithm.

20. The multi-modality navigation system of claim 16, wherein the imaging data processor processes the 3D volumetric US imaging data by applying at least one of a de-speckling, an edge detection or an amplitude scaling algorithm.

21. The multi-modality navigation system of claim 20, wherein the imaging data processor processes the 3D volumetric US imaging data by scaling a size of the 3D volumetric US imaging data to a size of the 3D volumetric non-US imaging data.

22. The multi-modality navigation system of claim 16, wherein the imaging data processor processes the 3D volumetric US imaging data and the 3D volumetric non-US imaging data by normalizing a total intensity of the 3D volumetric US imaging data and the 3D volumetric non-US imaging data.

23. The multi-modality navigation system of claim 16, wherein the markers include at least three co-planar anatomical markers.

* * * * *